United States Patent
Xiang et al.

(10) Patent No.: US 12,247,191 B2
(45) Date of Patent: Mar. 11, 2025

(54) ADJUSTABLE PLATE HOLDER FOR CELL CULTURES

(71) Applicants: Yang Xiang, Winchester, MA (US); Alexa Vahey, Peabody, MA (US); Aine Quimby, Newburyport, MA (US)

(72) Inventors: Yang Xiang, Winchester, MA (US); Alexa Vahey, Peabody, MA (US); Aine Quimby, Newburyport, MA (US)

(73) Assignee: AbClonal Science Inc., Woburn, MA (US)

( * ) Notice: Subject to any disclaimer, the term of this patent is extended or adjusted under 35 U.S.C. 154(b) by 892 days.

(21) Appl. No.: 17/391,727

(22) Filed: Aug. 2, 2021

(65) Prior Publication Data

US 2023/0033390 A1 Feb. 2, 2023

(51) Int. Cl.
*C12M 3/06* (2006.01)
*C12M 1/34* (2006.01)

(52) U.S. Cl.
CPC ............. *C12M 27/16* (2013.01); *C12M 41/46* (2013.01)

(58) Field of Classification Search
CPC ............................ C12M 27/16; C12M 41/46
USPC ............................................. 435/286.3
See application file for complete search history.

(56) References Cited

U.S. PATENT DOCUMENTS

| 6,660,232 B1 | 12/2003 | Krueger et al. |
| 6,808,304 B2 * | 10/2004 | Gebrian .................. B01F 31/24 366/110 |
| 11,020,474 B1 | 6/2021 | Xiang et al. |
| 2017/0312709 A1 * | 11/2017 | Duetz .................. B01F 31/265 |

FOREIGN PATENT DOCUMENTS

EP 2350613 B1 5/2015

* cited by examiner

Primary Examiner — Michael L Hobbs
Assistant Examiner — Lenora A Abel
(74) Attorney, Agent, or Firm — Eric P. Mirabel

(57) ABSTRACT

Disclosed is a device for angling a multi-well plate during shaking on a typical low speed laboratory incubator-shaker to facilitate cell growth. An assembly with a holder for a deep-well multi-well plate to attach it to a base has an adjustable-angle joint. The base is attached to a conventional incubator shaker tray via screws or a sticky pad. The adjustable-angle joint allows maintaining the desired angle of the plate, even at full shaking speed.

11 Claims, 4 Drawing Sheets

ADJUSTABLE PLATE HOLDER FOR CELL CULTURES

BACKGROUND

Ideally, culturing various cells (including bacteria, yeast, insect, or mammalian cells) in multi-well plates, specifically in deep multi-well plates, is widely performed for various assays and experiments. Multi-well plates are preferred for high-throughput procedures, as multi-well plates can accommodate robotic applications including pipetting samples or reagents, processing using multi-channel pipettes, and facilitated tracking and storing samples. Moreover, multi-well plates require significantly less bench-top space than test tubes on a rack.

Without rapid and continuous shaking, cell suspension cultures typically precipitate in the bottom of the wells, inhibiting cell growth due to limited nutrient availability in their locale. However, when cells are grown on a shaker tray that oscillates quickly in a circular horizontal plane, a superior suspension culture is achieved because there is more even distribution of nutrients to the growing cells. However, such high speed cell culture incubator-shakers are costly, and therefore unavailable to many labs.

Conventionally, multi-well plates are secured to an incubator's standard, low speed shaker tray via a sticky mat or by screws in order to secure the plate during shaking. This arrangement does not allow for the plate to be angled to the horizontal, similarly to the angling typically used when growing cultures in test tubes. When a well plate undergoes horizontal plane shaking at the low speeds typical for most laboratory incubator-shakers, the cells are prone to pelleting at the base of the wells, preventing proper culture growth, and limiting experimental output.

Thus, what is needed is a device for fast cell culturing and/or protein production which can be used with commonly available laboratory equipment.

SUMMARY

Angling a multi-well plate during shaking on a typical low speed laboratory incubator-shaker will facilitate cell growth. The invention includes an assembly with a holder for a deep-well multi-well plate to attach it to a base with an adjustable-angle joint, where the base is attached to a conventional incubator shaker tray via screws or a sticky pad. The adjustable-angle joint allows maintaining the desired angle of the plate, even at full shaking speed.

There is an optimal angle for a multi-well plate to maximize cell growth rate, which may change depending on cell type, reagents, temperature, shaking speed, and other conditions. The invention further includes a method of determining the optimal angle under different conditions, by running a variety of cell cultures of various types, under various conditions and angles for the plates, as a test set, and then determining the optimal plate angle for the various cell types and conditions; at a particular shaker speed. Different angles for the plate are expected to generate optimal production and/or growth rates for different cell cultures and conditions.

Angling the plate to the horizontal increases the surface area of liquids in the wells, compared to when the plate is horizontal. Greater liquid surface area increases the cell culture aeration, which may be a significant factor in enhancing cell growth or cell protein production rates. An angle of 45 degrees to the horizontal may produce optimal growth for a number of cell types and conditions, as that is the angle where liquid surface area is generally greatest. Lesser angles may still generate optimal cell growth or cell protein (including antibody) production rates, depending on cell type and other conditions, including reagents.

DETAILED DESCRIPTION

Figure 1A:
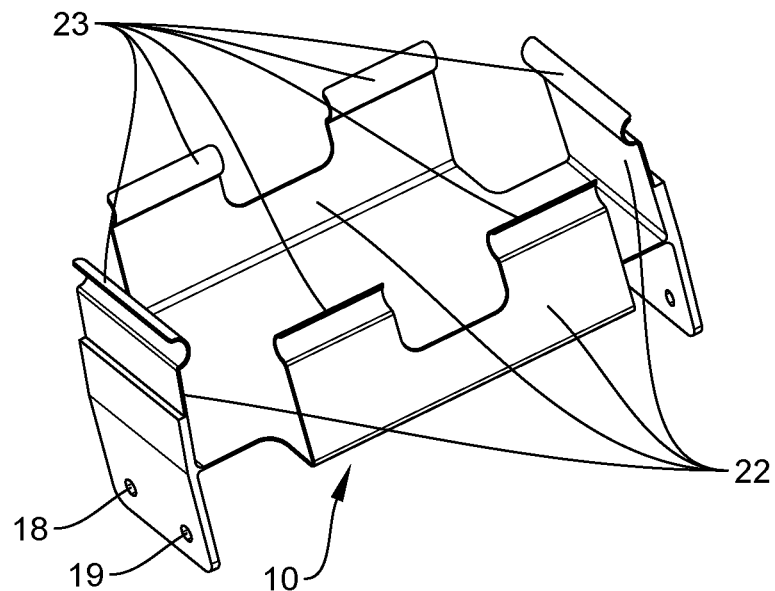
FIG. 1A is a perspective view of a plate holder of the invention.
Figure 1B:
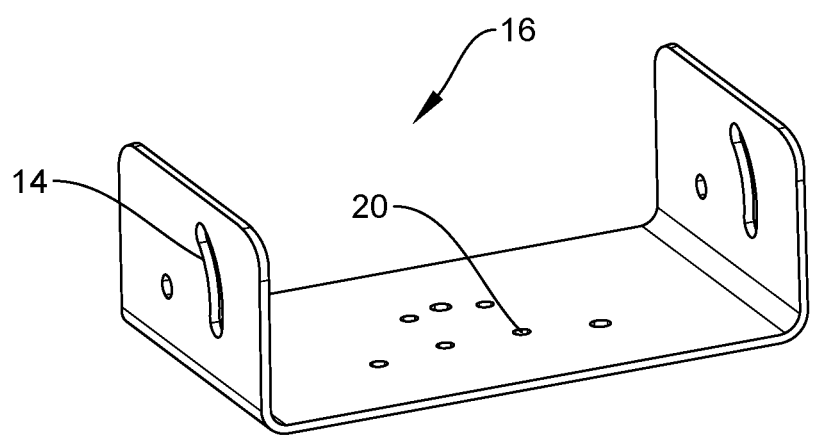
FIG. 1B is a perspective view of a base for the plate holder of FIG. 1A.
Figure 1C:
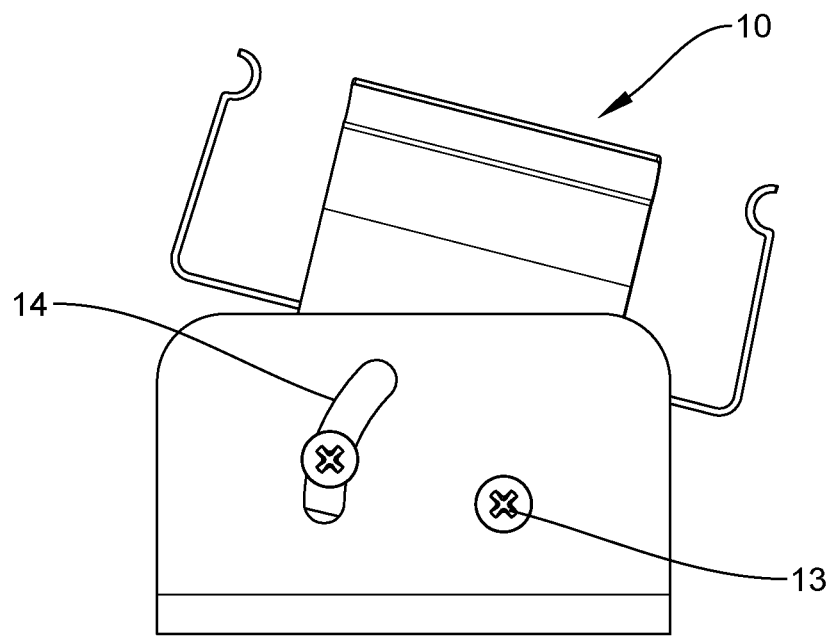
FIG. 1C is a side elevational view of the plate holder of FIG. 1A assembled with the base of FIG. 1B.
Figure 4:
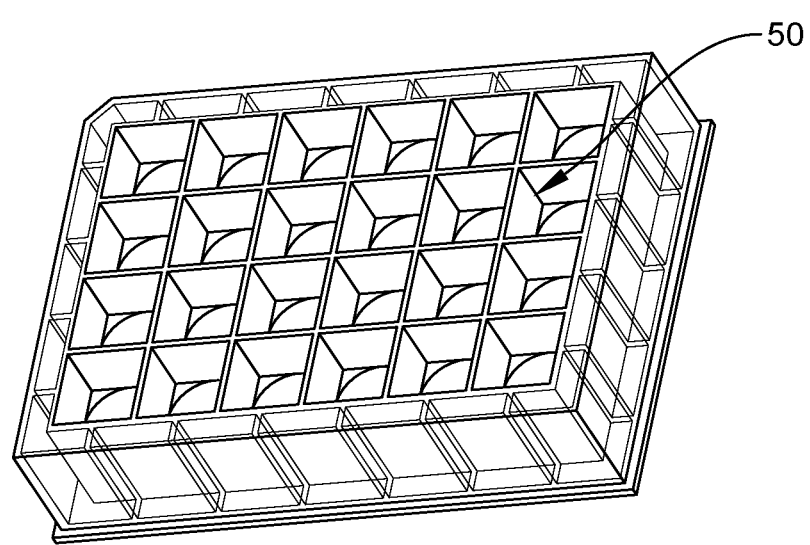
FIG. 4 shows a 24 well multi-well plate, which is held by the assembled device.

Referring to FIGS. 1A to 1C, a plate holder 10 includes side screws or bolts 12 and 13 which are accommodated by slots 14 in base 16. Screws or bolts 12 and 13 thread respectively into threaded holes 18 and 19 in base 16. Base 16 can be bolted or screwed to a shaker-tray (such as a shaker tray inside an incubator-shaker) by bolting or screwing it thereto through holes 20 in base 16; as shown in FIG. 4. Base 16 can also be glued to the shaker-tray in addition to or instead of bolting or screwing, or affixed to the shaker-try using a sticky pad (not shown).

Plate holder 10 accommodates and grips a multi-well plate 50 (see FIG. 5), using the using six arms 22 that angle in slightly towards each other, and each has a catch ridge 23 at the top to help grip the upper side of plate 50. Arms 22 are preferably sheet metal (more preferably steel) and flex outwardly slightly to accommodate the plate 50 then return to their original position and grip the sides of plate 50.

Figure 1D:
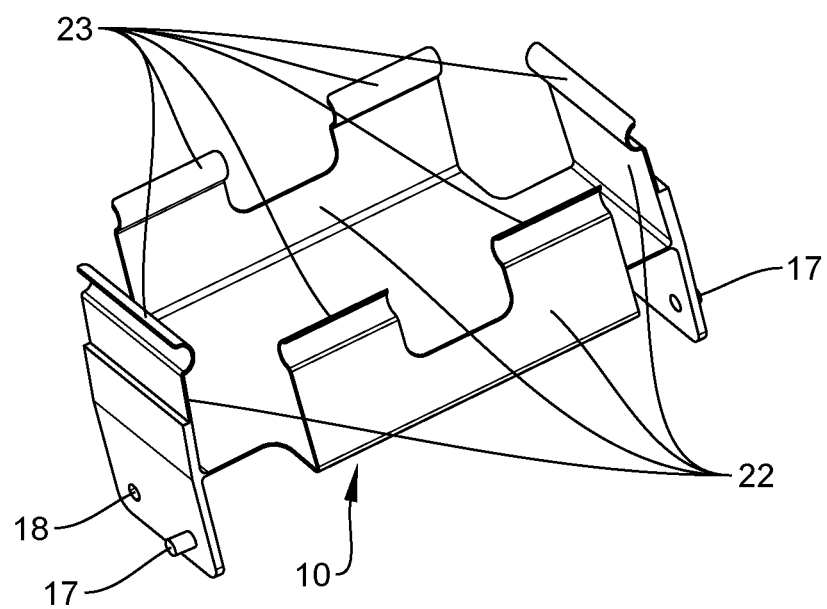
FIG. 1D is a perspective view of a different embodiment of the plate holder of the invention.
Figure 2:
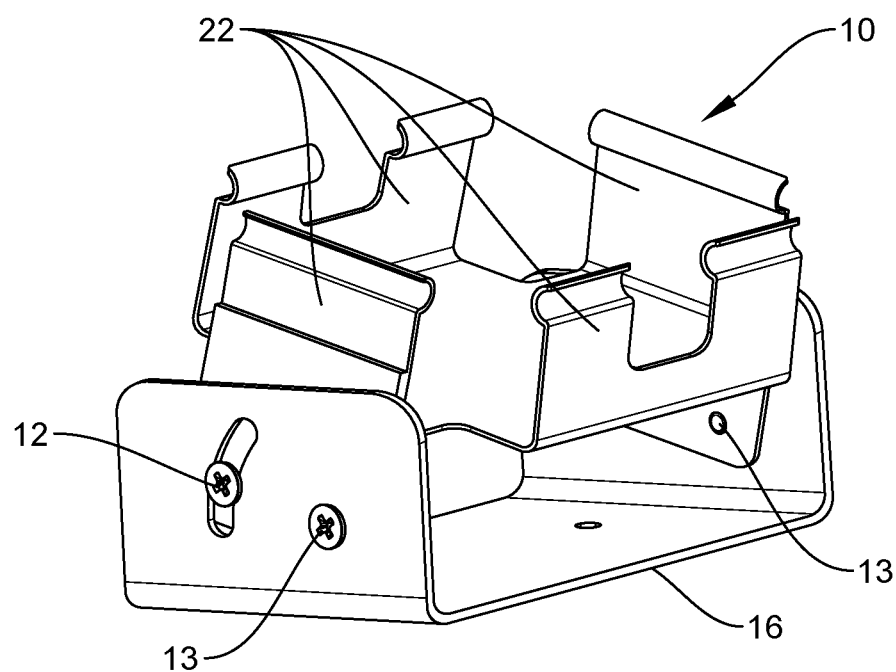
FIG. 2 is a perspective view of the assembled device showing the plate holder angled at about 24° to the horizontal.
Figure 3:
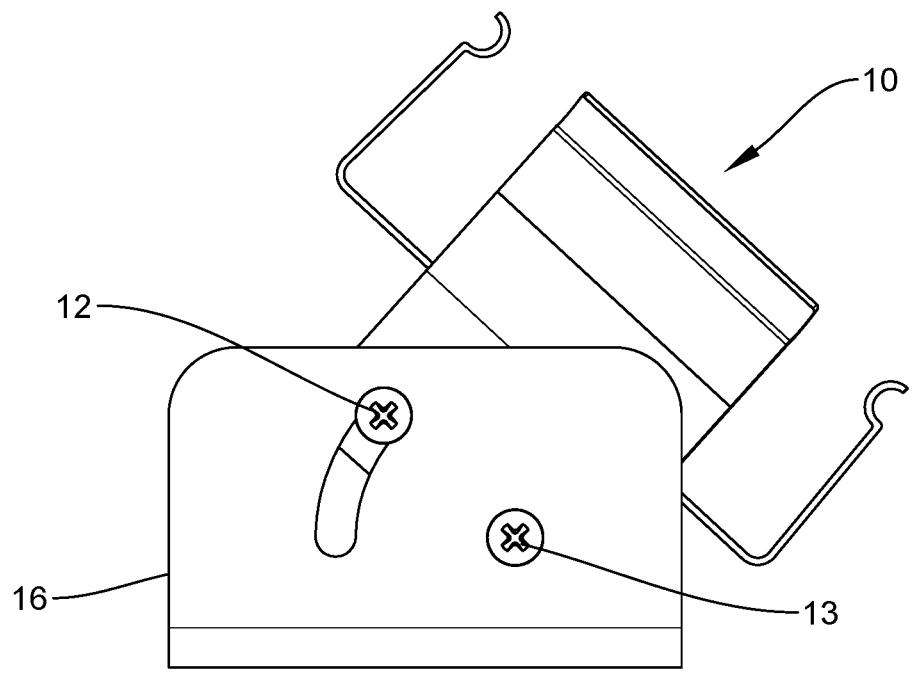
FIG. 3 is a side elevational view of the assembled device showing the plate holder angled at about 45° to the horizontal.

As seen in FIGS. 1C, 2 & 3, moving the plate holder 10 along slots 14 changes the angle of plate holder 10 (and therefore the wells in multi-well plate 50 when it's in place) relative to the horizontal, from about 0 degrees to a maximum of about 45 degrees. The angles of plate holder 10 can be fixed by tightening both screws 12 (one on each side) into threaded holes 18. One loosens screws 12 to change the angle of plate holder 10. It may also be necessary to loosen and tighten screws 13 to change the angle of plate holder 10. Alternatively, screws 13 can be replaced with a post 17 as in FIG. 1D so as to note require loosening and tightening when changing the plate holder 10 angle.

Regardless of angle of plate holder 10, with the device described and shown in the drawings, base 16 is securely affixed to the shaker and multi-well plate 50 is securely held by plate holder 10 at speeds attained by either standard or high-speed incubator-shakers. The invention allows cells to be grown in multi-well plates without test tubes and in a compact bench space.

Example I: Determining Optimal Plate Holder Angle

To determine the optimal plate angle to maximize cell growth for the various cell types and conditions, one first runs a variety of cell cultures of various types, under various conditions and angles for the plates, as a test set. The results are compiled and a variety of plate angles are used with various combinations of cell type, reagents, temperature, shaking speed, and then cell growth rate is determined for each different combination. The plate angle which optimizes cell growth rate for each combination is then identified, and the results are provided to the users of the invention for reference and use in cell culturing with the invention. If further experiments are performed which indicate modifications of the previous optimal angles should be substituted, these new angles can be provided to users of the invention wirelessly, by telephone or by internet communication.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

REFERENCES

EP2350613B1 An apparatus and a method for investigation of microtiter plates subjected to orbital shaking U.S. Pat. No. 6,660,232 Multi-well assay plate and plate holder and method of assembling the same U.S. Pat. No. 6,808,304 Method for mixing liquid samples using a linear oscillation stroke US Publ'n No. 20170312709A1 Orbital shaker U.S. Pat. No. 11,020,474 Producing recombinant SARS-CoV-2 spike protein in a pre-fusion state All the above references are incorporated by reference.

What is claimed is:

1. A device for angling a multi-well plate during shaking, comprising: a holder having a flat, planar holder floor and at least four holder arms angled towards each other and transverse to the holder floor, wherein at least a first two of the holder arms are opposed and each of said first two holder arms has at least a first threaded hole therein, and said first two holder arms also have either a second hole or a post extending away from and directly opposed one of the first two holder arms; and a base having a flat base floor and two opposed base arms each bearing at least one curved slot and at least one arm hole, wherein the base is dimensioned such that the two opposed base arms are positioned outside said first two holder arms, and the curved slots each align with one of the first threaded holes and each of the second holes align with one of the posts or one of the arm holes when the holder is placed in the base such that the holder floor and the base floor are placed immediately adjacent and aligned with each other.

2. The device of claim 1, further including at least two screws or bolts which each pass through one of the curved slots and thread into one of the first threaded holes.

3. The device of claim 1, wherein said first two holder arms each have the second hole and said second hole is threaded, and further including at least two screws or bolts which each thread into one of the second holes.

4. The device of claim 1, wherein said first two holder arms each have a ridge at an end distal to the holder floor which extends towards the opposing holder arm.

5. The device of claim 1, wherein the other two of the four holder arms which are not said first two holder arms each have a lower section and two upper sections each connected with the lower section.

6. The device of claim 5, wherein the upper sections each have a feature at an end distal to the holder floor which extends towards the opposing holder arm.

7. The device of claim 1, wherein the flat base floor has several holes in it.

8. A method of using a device of claim 1, to determine a optimal plate angle for shaking a multi-well plate held in the holder in order to maximize cell growth and/or protein production rates for the various cell types and conditions, comprising:

placing into each different well in the multi-well plate one particular cell type with a particular mix of cell growth reagent, such that different wells contain different particular cell types or different reagents;

setting the plate holder at a particular angle and a particular shaking speed, and determining cell growth and/or protein production rate in each well after shaking;

setting the plate holder at a number of different angles at a particular shaking speed, and determining cell growth and/or protein production rate in each well after shaking;

determining the optimal angle for the plate holder which is associated with the highest cell growth and/or protein production rate for each cell type when using the specific reagents in the same well as each cell type; and informing a party of the optimal angle for a particular cell type.

9. The method of claim 8, wherein the party is informed through wireless communication.

10. The method of claim 8, wherein the protein is an antibody.

11. The method of claim 8, wherein the protein is SARS-CoV-2 spike protein in a pre-fusion state.

\* \* \* \* \*